(12) United States Patent
Caden

(10) Patent No.: US 11,445,767 B2
(45) Date of Patent: *Sep. 20, 2022

(54) MOISTURE ABSORBING ANTI-LEAK UNDERGARMENTS

(71) Applicant: PROOF COMPANY, LLC, Sherman Oaks, CA (US)

(72) Inventor: Jodi Caden, Sherman Oaks, CA (US)

(73) Assignee: Proof Company, LLC, Sherman Oaks, CA (US)

( * ) Notice: Subject to any disclaimer, the term of this patent is extended or adjusted under 35 U.S.C. 154(b) by 183 days.

This patent is subject to a terminal disclaimer.

(21) Appl. No.: 17/002,187

(22) Filed: Aug. 25, 2020

(65) Prior Publication Data

US 2020/0383393 A1 Dec. 10, 2020

Related U.S. Application Data

(63) Continuation of application No. 15/969,705, filed on May 2, 2018, now Pat. No. 10,786,016.

(60) Provisional application No. 62/501,013, filed on May 3, 2017.

(51) Int. Cl.
| | | |
|---|---|---|
| A41C 3/00 | (2006.01) | |
| A41C 3/04 | (2006.01) | |
| B32B 27/06 | (2006.01) | |
| A61F 13/14 | (2006.01) | |
| A41B 9/12 | (2006.01) | |
| B32B 5/02 | (2006.01) | |
| B32B 27/40 | (2006.01) | |

(52) U.S. Cl.
CPC .............. *A41C 3/0057* (2013.01); *A41B 9/12* (2013.01); *A41C 3/04* (2013.01); *A61F 13/14* (2013.01); *A61F 13/141* (2013.01); *B32B 5/026* (2013.01); *B32B 27/06* (2013.01); *B32B 27/40* (2013.01); *A41B 2400/62* (2013.01); *A41C 3/0035* (2013.01); *B32B 2307/724* (2013.01); *B32B 2307/728* (2013.01); *B32B 2307/7265* (2013.01); *B32B 2307/73* (2013.01); *B32B 2437/00* (2013.01)

(58) Field of Classification Search
CPC ......... A41C 3/057; A41C 3/0035; A41C 3/04; A41B 9/12
USPC ...................................... 450/39, 36
See application file for complete search history.

(56) References Cited

U.S. PATENT DOCUMENTS

| | | | |
|---|---|---|---|
| 4,217,905 A | 8/1980 | Atwater et al. | |
| 4,875,492 A | 10/1989 | Mitchell et al. | |
| 5,441,436 A * | 8/1995 | Moretz ................. | A41B 9/02 450/38 |
| 6,083,080 A | 7/2000 | Lawson et al. | |
| 6,110,005 A | 8/2000 | Stephenson et al. | |
| 6,176,761 B1 | 1/2001 | Underhill | |

(Continued)

FOREIGN PATENT DOCUMENTS

EP      2879534 A1    6/2015

OTHER PUBLICATIONS

International Search Report and Written Opinion for PCT/US2018/030934; dated Jul. 11, 2018.

*Primary Examiner* — Gloria M Hale
(74) *Attorney, Agent, or Firm* — Stetina Brunda Garred and Brucker; Mark B. Garred

(57) ABSTRACT

Undergarments that are uniquely constructed to absorb fluids, such as those associated with sweat and lactation, in either prescribed areas of the undergarment or throughout the totality thereof.

11 Claims, 6 Drawing Sheets

(56) References Cited

U.S. PATENT DOCUMENTS

| | | | |
|---|---|---|---|
| 6,346,027 B1 | 2/2002 | Merkovsky | |
| 7,842,625 B1 | 11/2010 | Stockton et al. | |
| 8,117,675 B2 * | 2/2012 | Strange | A41B 17/00 2/400 |
| 8,460,265 B1 | 6/2013 | Calender | |
| 8,898,812 B2 | 12/2014 | Thompson et al. | |
| 9,781,954 B1 | 10/2017 | Osetek et al. | |
| 10,441,479 B2 | 10/2019 | Griffiths | |
| 10,786,016 B2 * | 9/2020 | Caden | B32B 27/06 |
| 2001/0019933 A1 | 9/2001 | Wagner | |
| 2003/0211810 A1 | 11/2003 | Raimondo | |
| 2006/0025039 A1 | 2/2006 | Barbour et al. | |
| 2007/0093162 A1 | 4/2007 | Holcombe et al. | |
| 2007/0155283 A1 | 7/2007 | McQueer | |
| 2008/0003922 A1 | 1/2008 | Hori | |
| 2008/0052802 A1 | 3/2008 | Bryan | |
| 2008/0096001 A1 | 4/2008 | Emden et al. | |
| 2008/0261489 A1 | 10/2008 | Sweeney | |
| 2009/0098803 A1 | 4/2009 | Reinisch et al. | |
| 2009/0203295 A1 * | 8/2009 | Kassel | A41C 3/04 604/385.07 |
| 2013/0316615 A1 * | 11/2013 | Hurd | A41D 31/125 264/45.3 |
| 2018/0317571 A1 | 11/2018 | Caden | |

\* cited by examiner

MOISTURE ABSORBING ANTI-LEAK UNDERGARMENTS

CROSS-REFERENCE TO RELATED APPLICATIONS

This application is a continuation of U.S. patent application Ser. No. 15/969,705 filed May 2, 2018 and entitled "MOISTURE ABSORBING ANTI-LEAK UNDERGARMENTS," now U.S. Pat. No. 10,786,016 issued Sep. 29, 2020, which relates to and claims the benefit of U.S. Provisional Application No. 62/501,013 filed May 3, 2017 and entitled "MOISTURE-WICKING ANTI-LEAK UNDERGARMENTS," the specification and drawings of which are provided as Appendix A hereto, incorporated herein by reference.

STATEMENT RE: FEDERALLY SPONSORED RESEARCH/DEVELOPMENT

Not Applicable

BACKGROUND

1. Technical Field

The present disclosure relates generally to wearing apparel and, more specifically, to undergarments that that are uniquely constructed to absorb fluids, such as those associated with sweat and lactation, in either prescribed areas of the undergarment or throughout the totality thereof.

2. Description of the Related Art

Undergarments may provide several functions, such as shaping the wearer's body, supporting parts of the body (e.g., during exercise), and offering protection to outer clothing. Undergarments can include everything from men's undershirts and women's brassieres or bras to their underwear.

Wearing a garment to support the chests or breasts may date back to ancient Greece. Women wore an apodesmos, later stēthodesmē, mastodesmos and mastodeton, all meaning "breast-band", a band of wool or linen that was wrapped across the chests or breasts and tied or pinned at the back. Fragments of linen textiles found in East Tyrol in Austria dated to between 1440 and 1485 are believed to have been bras. Two of them had cups made from two pieces of linen sewn with fabric that extended to the bottom of the torso with a row of six eyelets for fastening with a lace or string. One had two shoulder straps and was decorated with lace in the cleavage. From the 16th century, the undergarments of wealthier women in the Western world were dominated by the corset, which pushed the breasts upwards. In the later 19th century, clothing designers began experimenting with alternatives, splitting the corset into multiple parts: a girdle-like restraining device for the lower torso, and devices that suspended the breasts from the shoulder to the upper torso.

Women have played a large part in the design and manufacture of the bra, accounting for half the patents filed. The Dresden-based German Christine Hardt patented the first modern brassiere in 1899. Sigmund Lindauer from Stuttgart-Bad Cannstatt, Germany, developed a brassiere for mass production in 1912 and patented it in 1913. It was mass-produced by Mechanischen Trikotweberei Ludwig Maier and Cie. in Böblingen, Germany. In the United States, Mary Phelps Jacob received a patent in 1914 for the first brassiere design that is recognized as the basis for modern bras. Mass production in the early-20th century made the garment widely available to women in the United States, England, Western Europe, and other countries influenced by western fashion. Metal shortages in World War I encouraged the end of the corset. Bras were initially manufactured by small production companies and supplied to retailers. The term "cup" was not used until 1916, and manufacturers relied on stretchable cups to accommodate different sized breasts. Women with larger or pendulous breasts had the choice of long-line bras, built-up backs, wedge-shaped inserts between the cups, wider straps, power latex, firm bands under the cup, and light boning.

Typically, bras are form-fitting undergarments that perform the function of supporting a woman's breasts. Swimsuits, camisoles, and backless dresses may be made with built-in support. Bras are complex garments made of many parts, with standards and methods of measurement varying widely. Men's undershirts are also form-fitting undergarments.

A common problem faced by men and women is when they sweat due to hot flashes, other medical conditions such as hyperhidrosis, anxiety, etc., due to heat and other weather conditions, or because they have large breasts, the sweat seeps through the undergarments to their outer garment. Many people also suffer from primary local hyperhidrosis. The symptoms of primary focal hyperhidrosis are fairly specific. It's called "local" because it only affects specific parts of the body, such as the underarms, breasts/chest, groin, etc. Symptoms also tend to be symmetrical, occurring on both sides equally. Women, especially with bigger breasts, suffer from localized sweats, especially under their breasts. Many women have a tendency to perspire around their bra line, especially when under stress, at work, or when performing physical activity. Excessive unwanted perspiration can result in embarrassing odors, sweat stains, or eventually discoloration of the surrounding clothes. Excessive perspiration can also lead to the need to constantly wash the affected bras, which increases the amount of wear and tear on those bras and thus requires that they be replaced more often. It can be expensive to have to constantly replace worn down bras, especially for women with a unique bra size who must specially order bras to fit their specific measurements. A similar problem is also faced by men who have male breasts. However, conventional undergarments do not help prevent the seeping or transmission of sweat from the body of the wearer to the outer garment.

Another problem is leaking that is related to breastfeeding. For all of the known benefits of breastfeeding, one major challenge is leaking. Leaking or spraying breasts are a natural part of a woman's nursing experience. Leaking can occur when the milk ejection reflex ("MER"), also referred to as the let-down reflex, is unintentionally triggered by various stimuli outside of nursing. The breasts can leak colostrum (the milk produced right around childbirth, which is rich in protein and antibodies) or the breastmilk that is produced after the early colostrum period. Unintentional triggers of the MER can be a woman thinking about her baby, hearing a crying baby, or when her breasts become uncomfortably full—e.g., when a woman's baby starts going longer between feedings, she is in a situation where she isn't able to nurse as often as she usually does, the baby starts sleeping through the night, or she goes back to work and is not able to pump on a regular schedule. Sometimes, a warm shower can trigger a leak. And sometimes it can even happen while she is asleep. Some women experience leaking from one breast while they are nursing their baby on the other breast. In fact, a woman's breasts can continue to leak for weeks, months, or even years after she stops nursing.

Unfortunately, conventional bras do not help prevent the sweat and milk or colostrum from leaking out of the bra and onto the shirt because of inadequate absorbing features. The leaking of milk, colostrum, or even sweat creates stains on the undergarments and the outer shirts or other garments that are visible to the public. Additionally, especially during lactation, a woman's breasts are tender. Conventional bras do not have the soft padding that this tenderness requires, and thus are uncomfortable and/or hurt the woman's breasts while also not performing the required absorbing feature.

While various pads and the like have been developed to respond to various other perspiration or moisture problems (e.g., underarm shields, sanitary napkins, etc.) none have been developed with enough flexibility to address the needs of numerous varieties of women suffering from breast perspiration and/or milk leakage. It is acknowledged that other devices have been developed for wear under the breast, but they are purposefully relatively thick and bulky and either intended for cosmetic, uplift purposes. Other pads have been developed to absorb perspiration; however, they are either bulky, address mainly the area between the breasts, or address the entire under area of the breast from underarm to cleavage. Such pads are too bulky and obvious as to not provide discretion of wearing by the user.

Further, there are pads that are available that can be inserted between a woman's bra and her breasts during lactation. The available pads have limited use because the leak-proof barrier is generally in contact with the breast and nipples and may create irritation and soreness, particularly if the nipples stay too moist due to the wet pad being directly in touch with the breasts without any other insulating layers. The thick absorbent pad is bulky and uncomfortable to wear. Additionally, the leak-proof barrier and thick absorbent pad may entrap moisture within the undergarment, thereby increasing the risk of yeast infections.

Additionally, some pads are disposable and not reusable and the cost of purchasing the pads may be an economic burden since it may add up to a significant sum per year. Additionally, the waste produced is environmentally unsustainable. Moreover, the pads may be positioned incorrectly or sized incorrectly, which adds to their low efficacy and discomfort. Finally, the available pads are cumbersome to use since a woman must remember to put on and change her pads, or wash previously worn reusable ones, each time she has to use them.

Consequently, there is a need for undergarments, such as undershirts and bras, which eliminate the need for using disposable pads while effectively absorbing liquid flow and preventing sweat, leaked milk, and other bodily fluids from seeping through to the outer garment. Additionally, it is desirable that the undergarments provide stain prevention, moisture-wicking, antimicrobial management, and skin comfort. The present disclosure addresses these particular needs, as will be described in greater detail below.

BRIEF SUMMARY

In accordance with an exemplary embodiment of the present disclosure, there is provided a moisture absorbing undergarment comprising a body having a front section shaped to cover at least a portion of a wearer's chest area. The body is configured to be maintainable on the wearer's upper body such that the at least a portion of the wearer's chest area is covered by the front section.

The front section of the body is provided with a multi-layer construction. In greater detail, such construction includes a first layer fabricated from a soft, pliable material adapted to be placeable into contact with and provide a wicking effect drawing moisture from the wearer's chest area, a second layer disposed adjacent the first layer and fabricated from a material having prescribed moisture absorption properties, a third layer disposed adjacent the second layer and fabricated from an at least partially moisture blocking material, and a fourth layer disposed adjacent the third layer and fabricated from a material which defines an exteriorly presented surface of the front section and has prescribed aesthetic and tactile characteristics. The third layer is preferably laminated to the fourth layer, and may comprise a breathable, elastic polyurethane film. The second layer may be secured to the third layer via a prescribed attachment modality as maintains the second layer in substantially abutting contact with the third layer. Similarly, the first layer may be secured to the second layer via a prescribed attachment modality as maintains the first layer in substantially abutting contact with the second layer.

In the undergarment, the first layer may comprise a knit fabric having a first side positionable into contact with the wearer and a second side facing the second layer, with one or both of the first and second sides being treated with one of a hydrophilic composition and a hydrophobic composition. Along these lines, one of the first and seconds sides of the knit fabric may be treated with the hydrophilic composition, and the remaining one of the first and second sides is treated with the hydrophobic composition.

It is contemplated that within the undergarment, the first layer and the second layer may collectively define at least one pocket therebetween sized and configured to removably accommodate an ancillary absorption layer adapted to supplement the moisture absorption properties of the second layer.

It is further contemplated that, in one exemplary iteration of the undergarment, the body may further define an opposed pair of side sections generally positionable under respective ones of the wearer's arms, and a back section extensible along the wearer's back, with each of the front, side and backs sections is provided with the multi-layer construction. In accordance with a further contemplated refinement, the front section may define a pair of cup portions adapted to accommodate the wearer's breasts, a cradle portion which underlies the cup portions, and a center gore portion extending at least partially between the cup portions, with the cup, cradle and center gore portions each being provided with the multi-layer construction. With this particular construction, the first, second, third and fourth layers in each of the cradle and center gore portions may be operatively secured to each other in a manner which effectively maintains them in substantially abutting contact with each other, with the first layer and the second layer in each of the cup portions collectively define at least one pocket therebetween sized and configured to removably accommodate the aforementioned ancillary absorption layer adapted to supplement the moisture absorption properties of the second layer. Further, each of the cup portions may define a slot sized and configured to provide access into a respective one of the pockets.

The present disclosure is best understood by reference to the following detailed description when read in conjunction with the accompanying drawings.

BRIEF DESCRIPTION OF THE DRAWINGS

These, as well as other features of the present disclosure, will become more apparent upon reference to the drawings wherein.

Common reference numerals are used throughout the drawings and detailed description to indicate like elements.

DETAILED DESCRIPTION

Figure 1A:
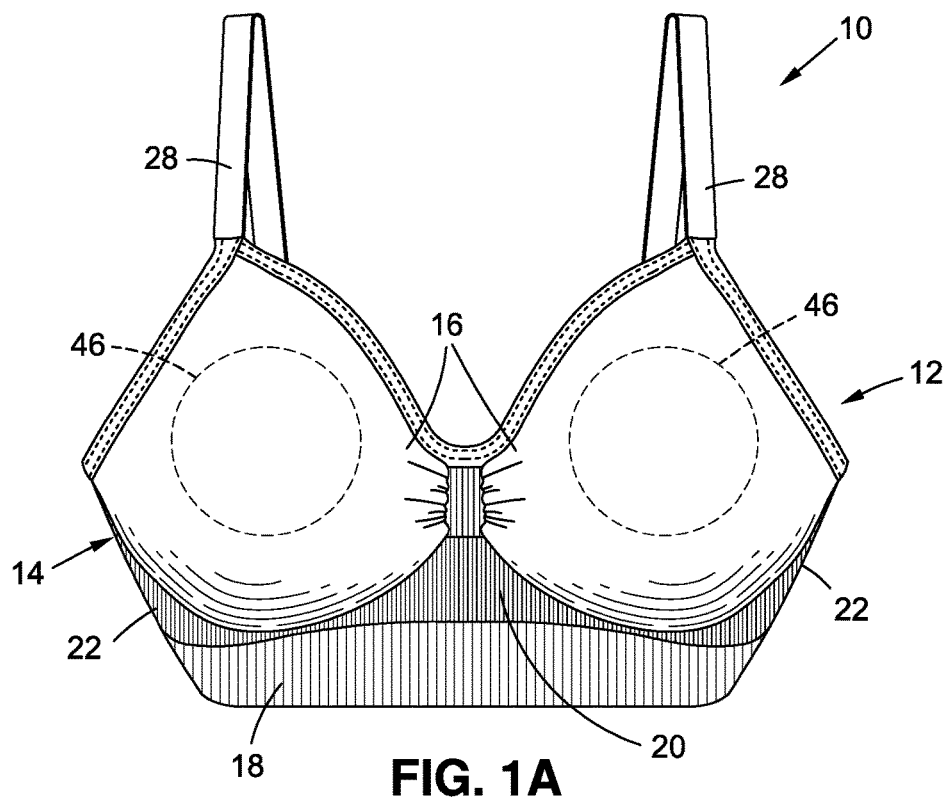
FIG. 1A is a front-elevational view of a first exemplary undergarment constructed in accordance with the present disclosure.
Figure 1B:
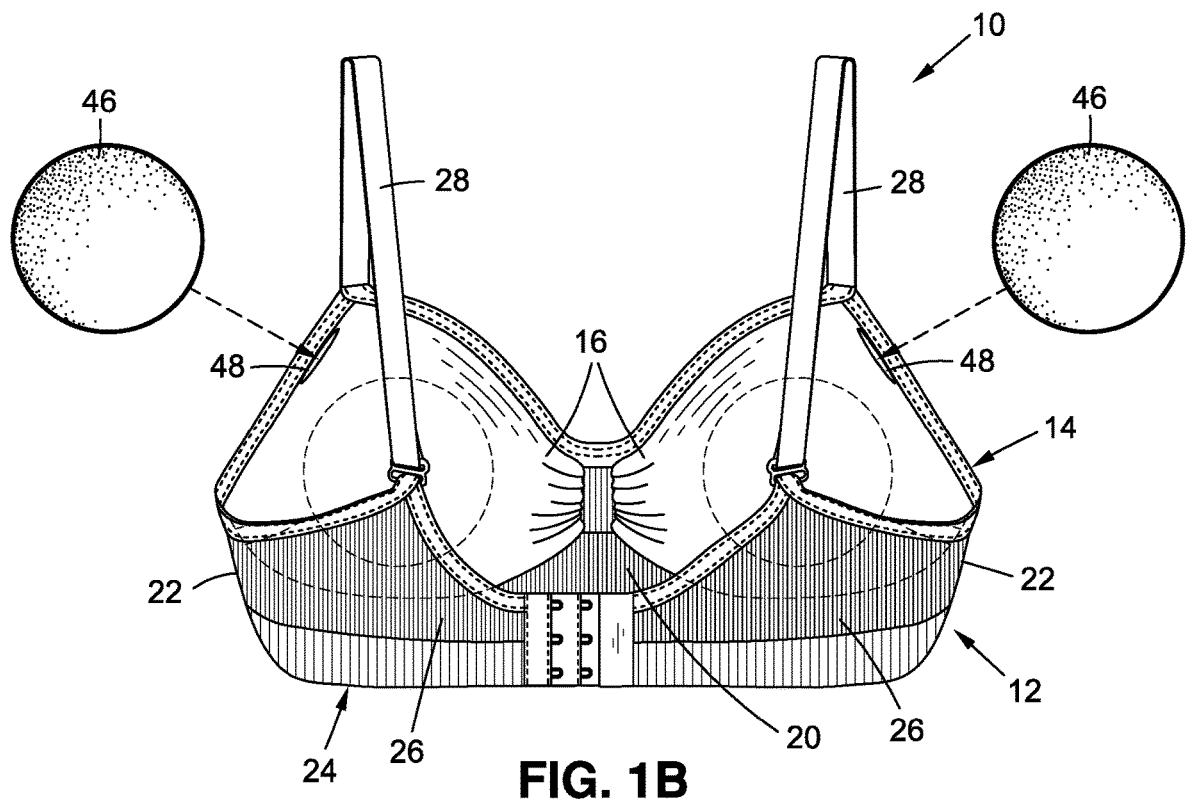
FIG. 1B is a rear-elevational view of the undergarment shown in FIG. 1A.
Figure 1C:
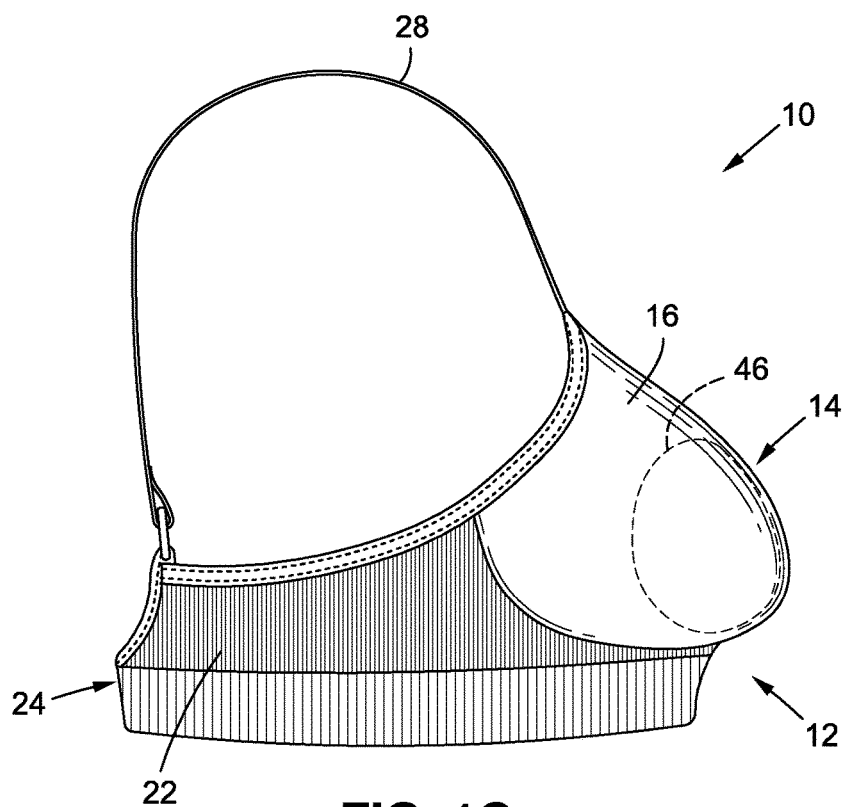
FIG. 1C is a right side-elevational view of the undergarment shown in FIG. 1A, the left side-elevational view being a mirror image thereof.

Referring now to the drawings wherein the showing are purposes of illustrating preferred implementations of the present disclosure only, and not for purposes of limiting the same, FIGS. 1A-1C depict a moisture absorbing undergarment 10 constructed in accordance with a first exemplary embodiment of the present disclosure. The undergarment 10 is a bra comprising a body 12. The body 12 includes a front section 14 shaped to cover at least a portion of a wearer's chest area. In greater detail, in the bra version of the undergarment 10 shown in FIGS. 1A-1C, the front section 14 defines several discrete regions. These regions include a spaced pair of cup portions 16 adapted to accommodate the wearer's breasts, a cradle portion 18 which underlies the cup portions 16, and a center gore portion 20 which extends at least partially between the cup portions 16.

As will be recognized by those of ordinary skill in the art, the body 14 is configured to be maintainable on the wearer's upper body such that the at least a portion of the wearer's chest area is covered by the front section 14. In the bra version of the undergarment 10, the body 14 further defines an opposed pair of side sections 22 generally positionable under respective ones of the wearer's arms, and a back section 24 extensible along the wearer's back. In the undergarment 10, the back section 24 is further segregated into an opposed, generally identical pair of wing segments 26 which are releasably attachable to each other. In the exemplary embodiment shown in FIG. 1B, the releasable attachment of the wing segments 26 to each other is facilitated by complementary sets of hooks and eyes. However, those of ordinary skill in the art will recognize that other, alternative fastening modalities, including but not limited to complementary snaps, clasps, hook and loop fastener material, etc., may be used to facilitate the releasable attachment of the wing sections 26 to each other without departing from the spirit and scope of the present disclosure.

The body 14 is further maintained upon the wearer's upper body through the use of a pair of identically configured straps 28 extensible over respective ones of the wearer's shoulders. As seen in FIGS. 1A-1C, each of the straps 28 includes a first (front) end attached to a respective one of the cup portions 18 of the front section 14, and an opposed second (back) end attached to a respective one of the wing segments 26 of the back section 24. Any one of numerous permanent or selectively releasable of attachment modalities (e.g., stitching, buckles, clasps, etc.) may be used to facilitate the attachment of the straps 28 to the remainder of the undergarment 10.

Figure 5:
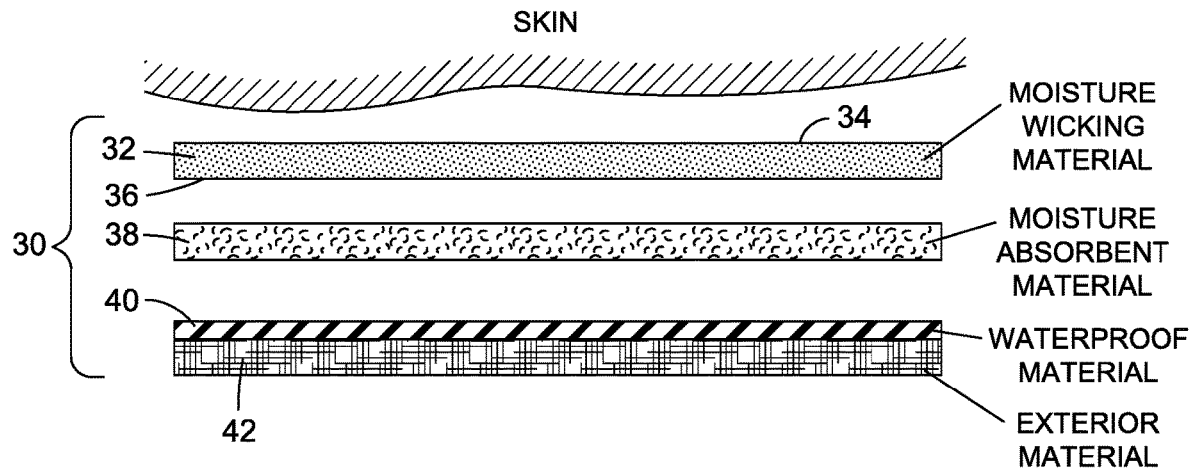
FIG. 5 is an exploded, cross-sectional view at least a portion of each of the exemplary undergarments shown in FIGS. 1A-1C and 2-4, depicting the multi-layer, moisture absorbing construction thereof.
Figure 6A:
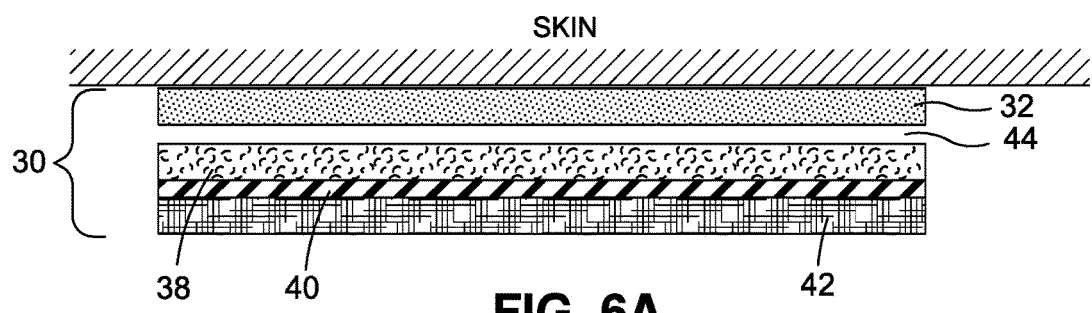
FIG. 6A is a cross-sectional view similar to FIG. 5, depicting a non-exploded, exemplary implementation of the multi-layer, moisture absorbing construction particularly suited to accommodate the optional, removable insertion of an ancillary absorption layer.
Figure 6B:
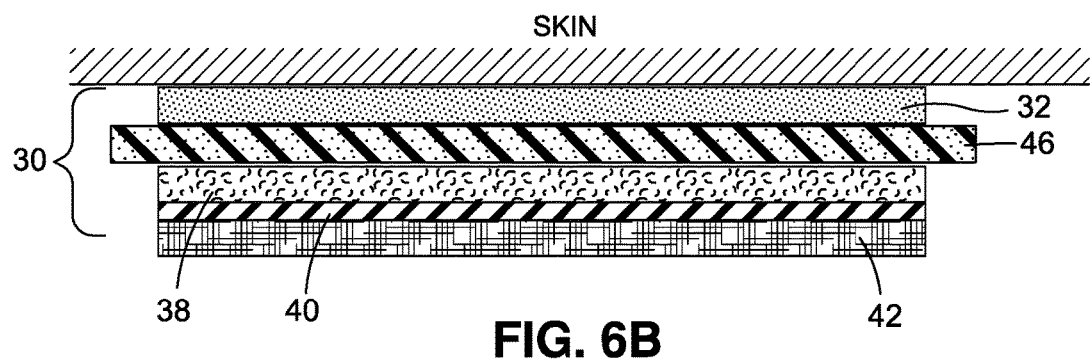
FIG. 6B is a cross-sectional view similar to FIG. 6A, but further depicting the ancillary absorption layer as removably inserted into the pocket defined within the multi-layer, moisture absorbing construction.

Referring now to FIGS. 5, 6A and 6B, in the undergarment 10, at least the front section 14 of the body 12 is provided with a multi-layer construction 30. It is contemplated that the form of the construction 30 that will be integrated into the undergarment 10 is that shown in FIGS. 6A and 6B, with FIG. 5 providing a more fully exploded view of that construction 30 for illustrative purposes. In greater detail, the construction 30 includes a first layer 32 fabricated from a soft, pliable material adapted to be placeable into contact with and provide a wicking effect drawing moisture from the wearer's chest area. In an exemplary implementation, the first layer 32 may comprise a knit fabric having a first side 34 positionable into contact with the wearer and an opposed second side 36. It is contemplated that one or both of the first and second sides 34, 36 may be treated with one of a hydrophilic composition and a hydrophobic composition. Alternatively, one of the first and seconds sides 34, 36 of the first layer 32 may be treated with the hydrophilic composition, with the remaining one of the first and second sides 34, 36 being treated with the hydrophobic composition. Further, the weave density of the knit fabric may be selected in accordance with desired wicking efficacy, the density being correlated to the size of moisture transmission paths defined through the knit fabric.

In addition to the first layer 32, the construction 30 comprises a second layer 38 which is disposed adjacent the first layer 32, the second side 36 of the first layer 32 thus facing the second layer 38. The second layer 38 is preferably fabricated from a material having prescribed moisture absorption properties. In an exemplary implementation, the second layer 38 is fabricated from a liquid or moisture absorbing material (e.g., cotton, a cotton blend, an absorbent foam, modal, viscose-based fiber, etc.) with a weight in the range of from about 180-300 $g/m^2$. However, those of ordinary skill in the art will recognize that other moisture absorbing materials provided in differing weights may be used for the second layer 38 without departing from the spirit and scope of the present disclosure.

The construction 30 further comprises a third layer 40 disposed adjacent the second layer 38. The third layer 40 is fabricated from an at least partially moisture blocking material. Also included in the construction 30 is a fourth layer 42 which is disposed adjacent the third layer 40 and fabricated from a material which defines an exteriorly presented surface of at least a portion of the front section 14, and has prescribed aesthetic and tactile characteristics. As seen in FIGS. 5, 6A and 6B, the third layer 40 is preferably laminated to the fourth layer 42, though it is also contemplated that such third and fourth layers 40, 42 need not necessarily be bonded to each other in the construction 30. In an exemplary implementation, the third layer 40 may comprise a breathable, elastic polyurethane film. Along these lines the composite structure achieved by the lamination of the third and fourth layers 40, 42 to each other, including materials which may be used for those third and fourth 40, 42 and techniques which may be employed to facilitate such lamination, can be selected in accordance with the teachings of Applicant's U.S. Pat. No. 8,117,675 entitled "Waterproof Panty" and issued Feb. 21, 2012, the entirety of which is incorporated herein by reference.

In the exemplary construction 30 as shown in FIGS. 6A and 6B, it is contemplated that the second layer 38 will be secured to the third layer 40 via a prescribed attachment modality as maintains the second layer 38 in substantially continuous, abutting contact with the third layer 40. Such attachment modalities may include stitching or adhesives, though the present disclosure is not intended to be limited to any particular modality. Along these lines, it is also understood that the attachment of the third and fourth layers 38, 40 to each other may be effectuated such that the contact therebetween is intermittent rather than substantially continuous. It is further contemplated that the construction 30 may be implemented in the manner shown in FIG. 5 wherein the third layer 38 is not attached or secured to the fourth layer 40, except at perhaps peripheral regions as may be necessary to complete the fabrication of the undergarment 10.

Though the third layer 38 is attached to the fourth layer 40 in the exemplary construction 30 shown in FIGS. 6A and 6B, it is contemplated that the first layer 32 will not be attached to the second layer 38, at least in prescribed areas of the front section 14, and notably the cup portions 16 of the front section 14. In this regard, in the undergarment 10, at least portions of the first and second layers 32, 38 collectively define at least one pocket 44 therebetween which is sized and configured to removably accommodate an ancillary absorption layer 46 adapted to supplement the moisture absorption properties of the second layer 38. In the undergarment 10, the construction 30 integrated into the front section 14 defines two separate and distinct pockets 44 centrally positioned within respective ones of the cup portions 16. Each pocket 44 is sized and configured to accommodate a respective ancillary absorption layer 46.

In the undergarment 10, each ancillary absorption layer 46 takes the form of a generally circular absorption pad. While each pad and its corresponding pocket 44 may have complementary circular configurations, sizes and shapes other than those shown in FIGS. 1A-1C are contemplated to be within the spirit and scope of the present disclosure. Additionally, each pad and its associated pocket 44 need not necessarily have complementary configurations. The absorption layer 46 (e.g., pad) may be fabricated from materials having prescribed moisture absorption properties, including but not limited to those described above in relation to the second layer 38. The material selection may be such that the absorption layer 46 may be subjected to repeated washings when removed from its corresponding pocket 44 without suffering rapid, undue degradation. Conversely, the absorption layer 46 may disposable. As seen in FIG. 1B, the undergarment 10 is provided with a pair of elongate slots or slits 48 within respective ones of the cup portions 16, each of which provides access to the interior of a respective one of the pockets 44 to allow for the advancement of the absorption layer 46 into its associated pocket 44, and removal of the absorption layer 46 from therewithin.

Figure 7:
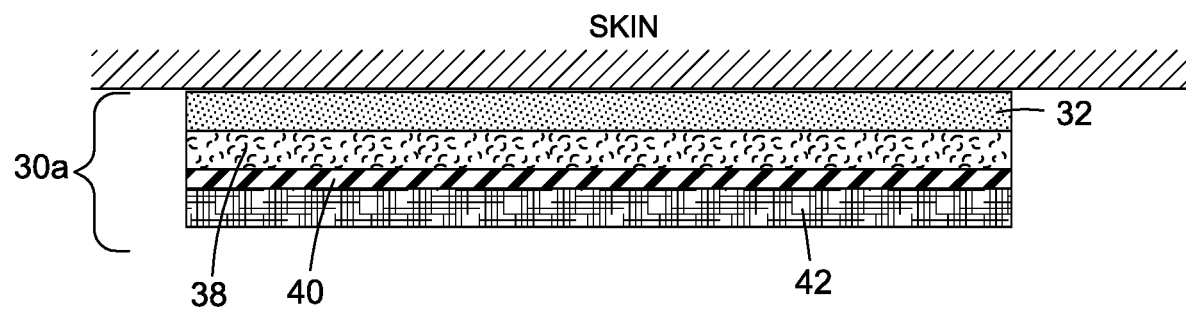
FIG. 7 is a cross-sectional view similar to FIGS. 6A and 6B, but depicting a first contemplated variant of the multi-layer, moisture absorbing construction shown therein.

Referring now to FIG. 7, there is shown a construction 30a which is a variant of the construction 30, and may be integrated into the undergarment 10 in substitution for or in addition to the construction 30. The sole distinction between the constructions 30, 30a lies in the first layer 32 in the construction 30a being secured to the second layer 38 via a prescribed attachment modality as maintains the first layer 32 in substantially continuous, abutting contact with the second layer 38, i.e., no pocket 44 is defined therebetween. Such attachment modalities may include stitching or adhesives, though the present disclosure is not intended to be limited to any particular modality. Along these lines, it is also understood that the attachment of the first and second layers 32, 38 to each other may be effectuated such that the contact therebetween is intermittent rather than substantially continuous.

Figure 8:
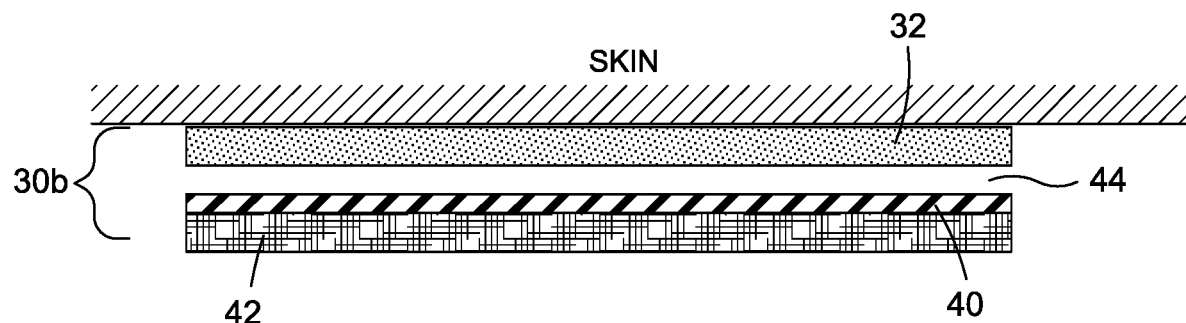
FIG. 8 is a cross-sectional view similar to FIGS. 6A and 6B, but depicting a second contemplated variant of the multi-layer, moisture absorbing construction shown therein.

Referring now to FIG. 8, there is shown a construction 30b which is another variant of the construction 30, and may itself be integrated into the undergarment 10 in substitution for or in addition to the construction 30. The sole distinction between the constructions 30, 30b lies in elimination of the second layer 38 in the construction 30b such that the pocket 44 is defined between the first and third layers 32, 40. Though not shown, yet a further variant of the construction 30 is contemplated wherein the construction 30b is modified such that the first layer 32 is secured to the third layer 40 via a prescribed attachment modality (such as those described above) as maintains the first layer 32 in substantially continuous, abutting contact with the third layer 40, i.e., no pocket 44 is defined therebetween.

As the chest/breast covering front section 14 of the undergarment 10 is that which is arguably the most essential to providing the moisture absorbing properties of the present disclosure, it follows that a typical implementation of the undergarment 10 will entail fabricating at least the cup portions 16 from either the construction 30 (with the two pockets 44), the construction 30a (with no pockets 44), the construction 30b (with no second layer 38 but with two pockets 44), or the aforementioned variant of the construction 30b (with no second layer 38 and no pockets 44). However, it is also contemplated that other parts of the undergarment 10 other than for the cup portions 16 may be fabricated from some iteration of the multi-layer construction, albeit typically one without pockets 44 (such as the construction 30a or variant of the construction 30b) to provide moisture/perspiration absorbing and/or transmission blocking qualities. By way of example, areas of the undergarment 10 susceptible to perspiration exposure, such as the cradle portion 18 which underlies the cup portions 16, the center gore portion 20, the side sections 22, and the back section 24 may, in addition to the cup portions 16, be fabricated from any one or more multi-layer construction iterations alone or in any combination.

Also, as is apparent from FIGS. 1A-1C, assuming several different multi-layer constructions are integrated into the undergarment 10 in prescribed locations thereof, it is contemplated that the exteriorly presented layer included in each such construction (i.e., the layer 42) may differ based on aesthetic, tactile, or other preferences/considerations. For example, as shown in FIG. 1A, the layer 42 of the multi-layer construction used for the cup portions 16 may differ the layer 42 of the multi-layer construction used for the cradle portion 18, which in turn may differ from the layer 42 of the multi-layer construction used for the center gore portion 20.

Figure 2:
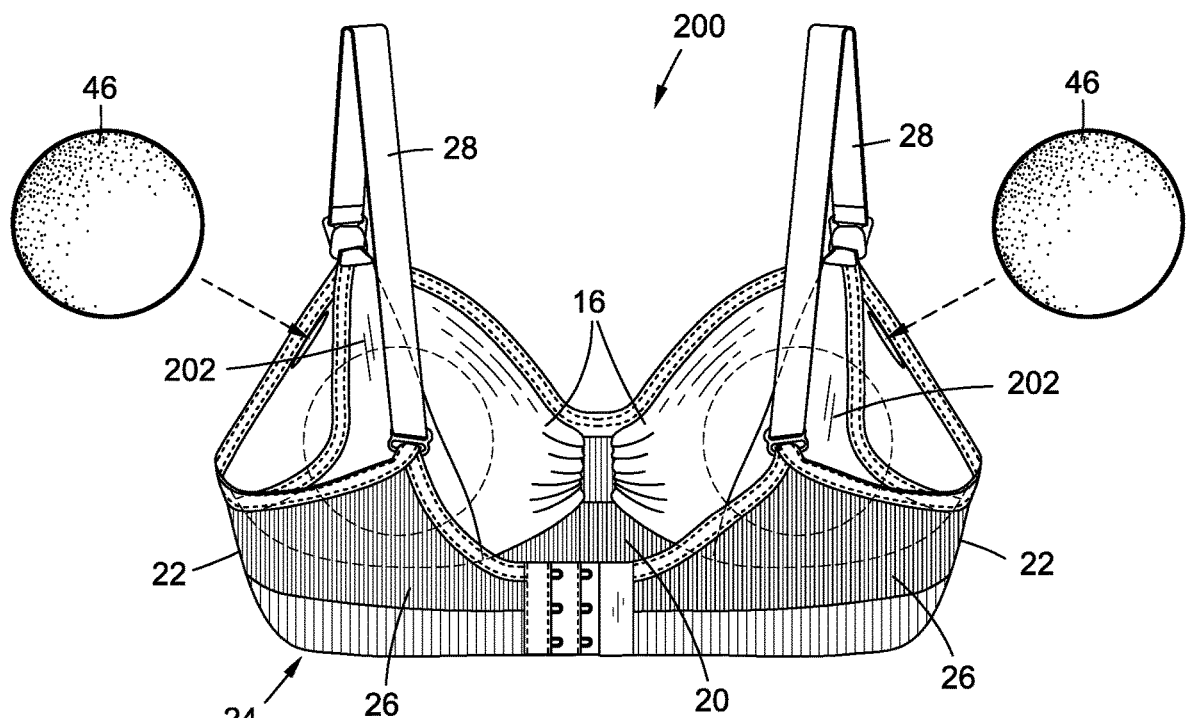
FIG. 2 is a rear-elevational view of a second exemplary undergarment constructed in accordance with the present disclosure.

Referring now to FIG. 2, there is shown a second exemplary undergarment 200 which may be fabricated to include any of the aforementioned iterations of the multi-layer construction in any of the aforementioned combinations. In this regard, the undergarment 200 differs from the undergarment 10 described above only in that it comprises a nursing bra wherein the cup portions 16 are releasably engaged to respective ones of the straps 28 as allows them to be selectively folded downwardly as the undergarment 200 is being worn. The straps are further attached to respective ones of pair of support panels 202 which are operative to maintain the undergarment 200 on the upper body of the wearer when either or both of the cup portions 16 are detached from the corresponding one of the straps 28.

Figure 3A:
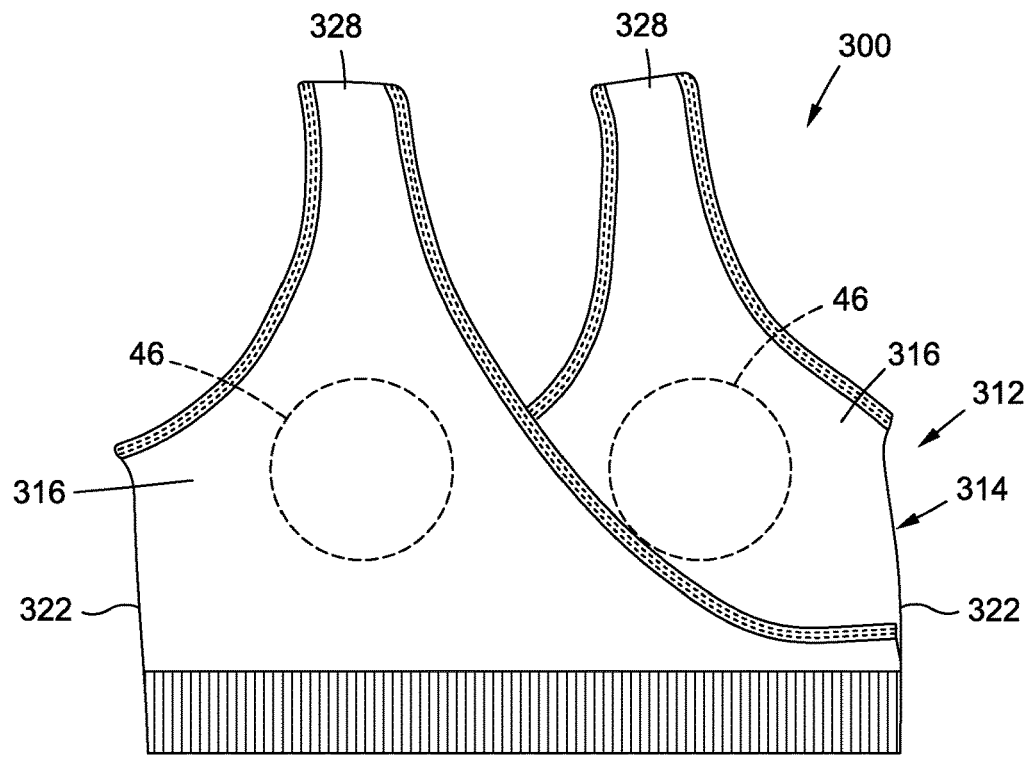
FIG. 3A is a front-elevational view of a third exemplary undergarment constructed in accordance with the present disclosure.
Figure 3B:
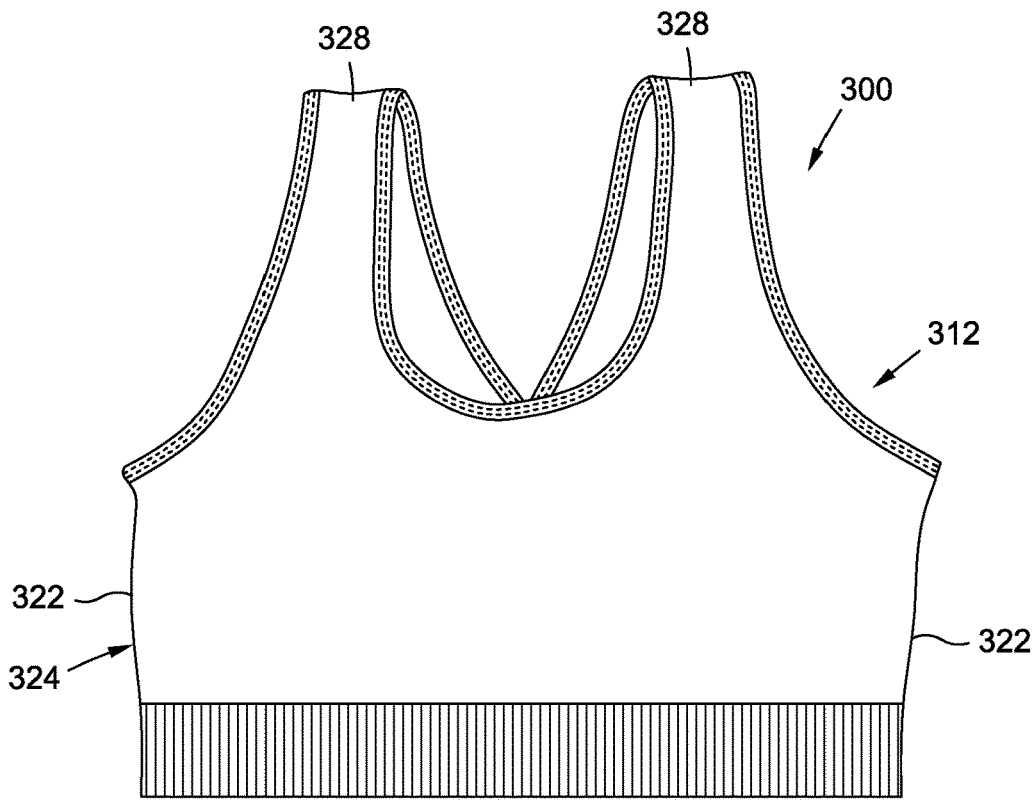
FIG. 3B is a rear-elevational view of the undergarment shown in FIG. 3A.

Referring now to FIGS. 3A and 3B, there is shown a third exemplary undergarment 300 which may also be fabricated to include any of the aforementioned iterations of the multi-layer construction in any of the aforementioned combinations. In this regard, the undergarment 300 differs from the undergarment 10 described above in that it comprises a nursing sleep bra having a body 312 with a front section 314 predominantly defined by a partially overlapping pair of cup panels 316 in substitution for the cup portions 16 shown in FIGS. 1A-1C and 2 above. The body 312 also includes a back section 324, a pair of shoulder sections 328 which are each adapted to span a respective one of the wearer's shoulders and define continuous transitions from respective ones of the cup panels 316 to the back section 324, and an opposed pair of side sections 322 which also define continuous transitions from respective ones of the cup panels 316 to the back section 324. Each of these panels/sections is amenable to having any iteration of the multi-layer construction integrated therein. In the exemplary iteration shown in FIG. 3A, each of the cup panels 316 is fabricated in accordance with the construction 30, and thus includes the pockets 44 which accommodate respective absorption layers 46/pads.

Figure 4A:
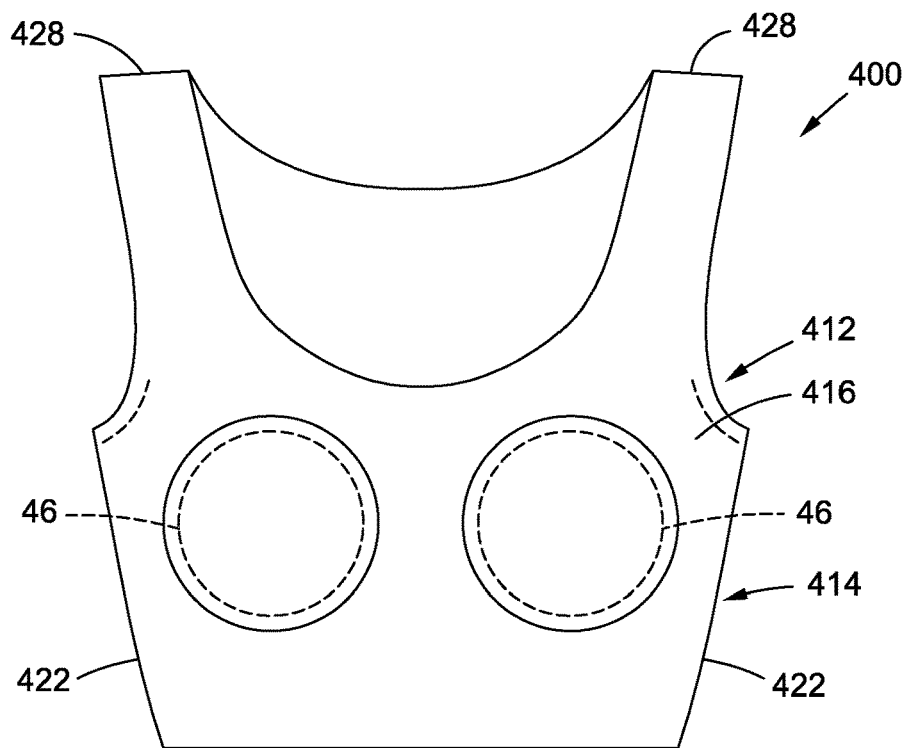
FIG. 4A is a front-elevational view of a fourth exemplary undergarment constructed in accordance with the present disclosure.
Figure 4B:
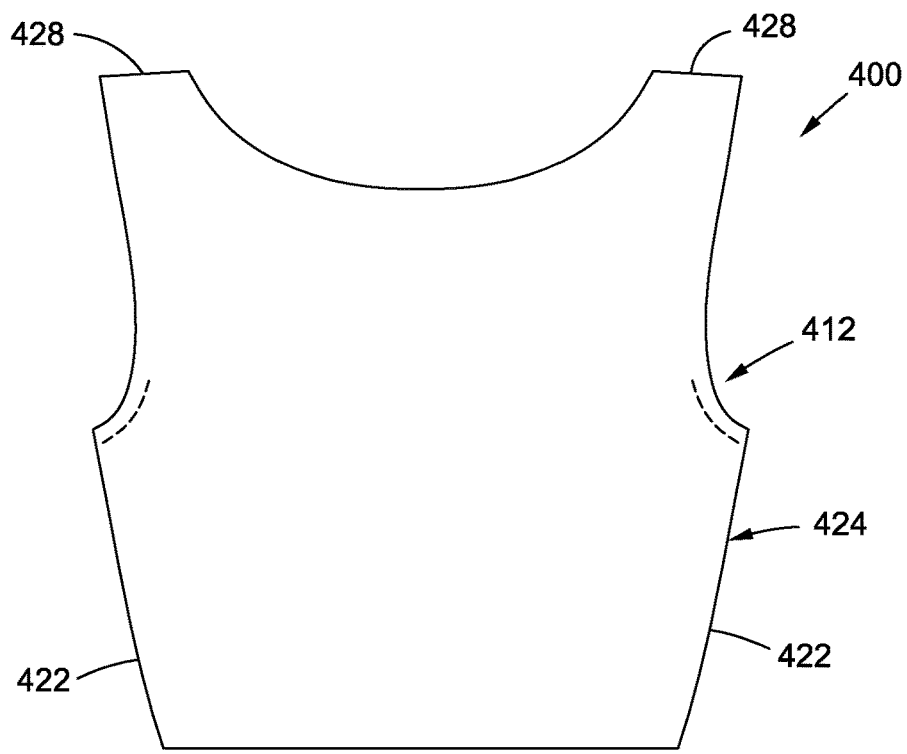
FIG. 4B is a rear-elevational view of the undergarment shown in FIG. 3A.

Referring now to FIGS. 4A and 4B, there is shown a fourth exemplary undergarment 400 which may also be fabricated to include any of the aforementioned iterations of the multi-layer construction in any of the aforementioned combinations. In this regard, the undergarment 400 differs from the undergarment 10 described above in that it comprises a sports bra having a body 412 with a front section 414 predominantly defined by a breast covering region 416 in substitution for the cup portions 16 shown in FIGS. 1A-1C and 2 above. The body 412 also includes a back section 424, a pair of shoulder sections 428 which are each adapted to span a respective one of the wearer's shoulders and define continuous transitions from the front section 414 to the back section 424, and an opposed pair of side sections 422 which also define continuous transitions from the front section 414 to the back section 424. Each of these sections is amenable to having any iteration of the multi-layer construction integrated therein. In the exemplary iteration shown in FIG. 4A, at least the breast covering region 416 of the front section 414 is fabricated in accordance with the construction 30, and thus includes the pockets 44 which accommodate respective absorption layers 46/pads. However, in the context of the undergarment 400 wherein the breast covering region 416 is substantially continuous, it is possible that a single pocket 44 may be defined therein which accommodates a single absorption layer 46/pad of suitable size to span both the wearer's breasts.

Though not shown, those of ordinary skill in the art will recognize that any of the aforementioned iterations of the multi-layer construction may be integrated in any of the aforementioned combinations into corresponding areas or regions of wearing apparel items other than for undergarments, including tank tops, T-shirts, etc., without departing from the spirit and scope of the present disclosure.

In various alternative embodiments, the materials described in specific embodiments herein may be substituted by materials that would be recognizable as compatible by those skilled in the art. Further, any chemicals, compounds, stains, dyes, and other treatments or elements of the garment, its design, or the process by which it is created may be substituted with other known materials recognized by those skilled in art, including but not limited to hydrophilic elements, hydrophobic elements, sealants, foams, and others. The various components or subparts of any embodiment may also be substituted and used with other subparts of other embodiments and various combinations thereof provided the claimed functionalities or general purpose of the design is preserved. Along these lines, all features, elements, components, functions, and steps described with respect to any embodiment provided herein are intended to be freely combinable and substitutable with those from any other embodiment unless otherwise stated. Thus, this disclosure provides exemplary embodiments, the scope of the present disclosure not being limited by these exemplary embodiments, with numerous variations, whether explicitly provided for by the specification or implied by the specification, such as variations in structure, dimension, type of material and manufacturing process, being capable of implementation by one of skill in the art in view of this disclosure.

What is claimed is:

1. A reusable, moisture absorbing garment, comprising:
   a body comprising a front section and a back section shaped to cover a portion of a wearer's anatomy, the body being configured to be independently maintainable on the wearer such that a prescribed portion of the wearer's anatomy is covered by the front section;
   at least a portion of the front section of the body being provided with a multi-layer construction including:
      a first layer fabricated from a soft, pliable material adapted to be placeable into contact with and provide a wicking effect drawing moisture from the wearer's anatomy;
      a second layer disposed adjacent the first layer and fabricated from a material having prescribed moisture absorption properties; and
      a third layer disposed adjacent the second layer and fabricated from an at least partially moisture blocking material;
   at least a portion of the back section of the body being provided with a multi-layer construction including:
      a first layer fabricated from a soft, pliable material adapted to be placeable into contact with the wearer and provide a wicking effect; and
      a second layer disposed adjacent the first layer and fabricated from an at least partially moisture blocking material.

2. The garment of claim 1 wherein at least portions of the first and second layers in the back section are secured to each other via a prescribed attachment modality as maintains the first layer of the back section in substantially abutting contact with the second layer thereof.

3. The garment of claim 1 wherein at least portions of the second and third layers in the front section are secured to each other via a prescribed attachment modality as maintains the second layer of the front section in substantially abutting contact with the third layer thereof.

4. The garment of claim 3 wherein at least portions of the first and second layers in the front section are secured to each other via a prescribed attachment modality as maintains the first layer of the front section in substantially abutting contact with the second layer thereof.

5. The garment of claim 1 wherein at least portions of the first and second layers in the front section are secured to each other via a prescribed attachment modality as maintains the first layer of the front section in substantially abutting contact with the second layer thereof.

6. The garment of claim 1 wherein the first layer of each of the front and back sections comprises a fabric having a first side positionable into contact with the wearer and a second side facing the second layer, with one or both of the first and second sides being treated with one of a hydrophilic composition and a hydrophobic composition.

7. The garment of claim 6 wherein one of the first and seconds sides of the fabric is treated with the hydrophilic composition, and the remaining one of the first and second sides is treated with the hydrophobic composition.

8. The garment of claim 1 wherein the first layer and second layers in the front section collectively define at least one pocket therebetween sized and configured to optionally, removably accommodate an ancillary absorption layer adapted to supplement the moisture absorption properties of the second layer of the front section by absorbing moisture transmitted through the first layer toward the second layer in the front section.

9. The garment of claim 1 wherein:
the front section defines a pair of cup portions adapted to accommodate the wearer's breasts, and a cradle portion which underlies the cup portions; and
the cup and cradle portions are each provided with the multi-layer construction including the first, second and third layers.

10. The garment of claim 9 wherein:
the first, second, and third layers in the cradle portion are operatively secured to each other in a manner which effectively maintains them in substantially abutting contact with each other; and
the first and second layers in each of the cup portions collectively define at least one pocket therebetween sized and configured to optionally, removably accommodate an ancillary absorption layer adapted to supplement the moisture absorption properties of the second layer of the front section by absorbing moisture transmitted through the first layer toward the second layer in the front section.

11. The garment of claim 10 wherein each of the cup portions defines a slot sized and configured to provide access into a respective one of the pockets.

* * * * *